United States Patent
Souza et al.

(10) Patent No.: US 11,661,396 B2
(45) Date of Patent: May 30, 2023

(54) CRYSTALLINE FORMS OF ZUCLOMIPHENE CITRATE

(71) Applicant: Apotex Inc., Toronto (CA)

(72) Inventors: Fabio E. S. Souza, Brantford (CA); Mohammed Abdul Raheem, Brantford (CA); Yajun Zhao, Brantford (CA); Siva Ramarao Kakani, Brantford (CA); Minh T. N. Nguyen, Brantford (CA); Alexander J. Stirk, Brantford (CA); Allan W. Rey, Brantford (CA); Stuart P. Green, Brantford (CA)

(73) Assignee: Apotex Inc., Toronto (CA)

( * ) Notice: Subject to any disclaimer, the term of this patent is extended or adjusted under 35 U.S.C. 154(b) by 116 days.

(21) Appl. No.: 17/154,261

(22) Filed: Jan. 21, 2021

(65) Prior Publication Data
US 2021/0221767 A1    Jul. 22, 2021

Related U.S. Application Data

(60) Provisional application No. 62/964,354, filed on Jan. 22, 2020.

(51) Int. Cl.
*C07C 217/48* (2006.01)

(52) U.S. Cl.
CPC ........ *C07C 217/48* (2013.01); *C07B 2200/13* (2013.01)

(58) Field of Classification Search
CPC ... C07C 217/48; C07C 59/265; C07C 217/18; C07B 2200/13; A61P 35/00
See application file for complete search history.

(56) References Cited

U.S. PATENT DOCUMENTS

| | | | |
|---|---|---|---|
| 2,914,563 | A | 11/1959 | Allen et al. |
| 3,848,030 | A | 11/1974 | Viterbo et al. |
| 9,428,442 | B2 | 8/2016 | Serafini et al. |
| 9,913,815 | B2 | 3/2018 | Steiner et al. |
| 9,914,696 | B2 | 3/2018 | Podolski et al. |

(Continued)

FOREIGN PATENT DOCUMENTS

| | | |
|---|---|---|
| FR | 3082842 A | 12/2019 |
| GB | 1099093 | 1/1968 |

(Continued)

OTHER PUBLICATIONS

Bernstein. Polymorphism in Molecular Crystals, Oxford University Press, New York, 2002, p. 9 (Year: 2002).*

(Continued)

*Primary Examiner* — Mark L Shibuya
*Assistant Examiner* — Luisalberto Gonzalez
(74) *Attorney, Agent, or Firm* — The Webb Law Firm

(57) ABSTRACT

The present invention provides novel crystalline forms of zuclomiphene citrate. Specific crystalline forms provided by the present invention include zuclomiphene citrate Forms APO-I, APO-II, APO-III, and APO-IV. Also provided are pharmaceutical compositions including the zuclomiphene citrate crystalline forms, processes for the preparation thereof and the use of these forms in the treatment of a disorder selected from the group including osteoporosis, bone fractures, loss of bone mineral density (BMD) and hot flashes in a subject suffering therefrom.

23 Claims, 8 Drawing Sheets

(56) References Cited

U.S. PATENT DOCUMENTS

| | | | |
|---|---|---|---|
| 2015/0202167 A1 | 7/2015 | Podolski et al. | |
| 2017/0349533 A1* | 12/2017 | Padovan | ............... C07C 217/54 |

FOREIGN PATENT DOCUMENTS

| | | | | |
|---|---|---|---|---|
| WO | 2014031177 A1 | 2/2014 | | |
| WO | WO-2014031177 A1 * | 2/2014 | ........... | A61K 31/138 |
| WO | 2016014812 A1 | 1/2016 | | |
| WO | 2016106189 A1 | 6/2016 | | |

OTHER PUBLICATIONS

Al-Hassan, "Synthesis of Clomid Using Palladium-Catalyzed Cross-Coupling, Synthetic Communications: An International Journal for Rapid Communication of Synthetic Organic Chemistry," 1987, pp. 1787-1796, 17 (15).

Barber et al., "Nickel-Catalyzed Hydroarylation of Alkynes under Reductive Conditions with Aryl Bromides and Water," J. Org. Chem., 2019, pp. 11612-11622, vol. 84.

Bernstein, "Is this material polymorphic?," Polymorphism in Molecular Crystals, 2002, p. 9, Oxford University Press, New York.

Crenshaw et al., "Synthesis of Trisubstituted Vinyl Chlorides," J. Org. Chem., 1983, pp. 2782-2784, 48 (16).

Dolginova et al., "Synthesis and Biological Study of the cis- and trans-Isomers of Clomiphene Citrate and Some Intermediates of its Synthesis," Pharm. Chem. J. ,1984, pp. 758-764, 11.

Palopoli et al., "Substituted Aminoalkoxytriarylhaloethylenes," J. Med. Chem., 1967, pp. 84-86, vol. 10 (1).

Porter, "Coating of Pharmaceutical Dosage Forms," Remington The Science and Practice of Pharmacy 21st Edition, 2006, Chapter 46, pp. 929-938, Lippincott Williams & Wilkins, Philadelphia.

Rudnic et al., "Oral Solid Dosage Forms," Remington The Science and Practice of Pharmacy 21st Edition, 2006, Chapter 45, pp. 889-928, Lippincott Williams & Wilkins, Philadelphia.

Stahl et al. (eds.), Handbook of Pharmaceutical Salts Properties, Selection, and Use, 2002, Appendix, pp. 329-345, Verlag Helvetica Chimica Acta, Zurich.

Veru, Inc., "Veru Announces Positive Top-Line Interim Data from Phase 2 Clinical Trial of Zuclomiphene to Treat Hot Flashes in Men with Prostate Cancer on Androgen Deprivation Therapy," Veru Inc. press release, Jan. 13, 2020. On the Veru Inc. website, https://verupharma.com/news/, accessed Jan. 14, 2020.

* cited by examiner

CRYSTALLINE FORMS OF ZUCLOMIPHENE CITRATE

CROSS-REFERENCE TO RELATED APPLICATION

This application claims priority to U.S. Provisional Patent Application No. 62/964,354 filed Jan. 22, 2020, the disclosure of which is hereby incorporated by reference in its entirety.

BACKGROUND OF THE INVENTION

Field of the Invention

The present invention is directed to novel crystalline forms of zuclomiphene citrate, processes for the preparation thereof, pharmaceutical compositions containing these forms, and their use for the treatment of a disorder selected from the group consisting of osteoporosis, bone fractures, loss of bone mineral density (BMD) and hot flashes in a subject suffering therefrom.

Description of Related Art

Clomid®, a drug initially approved by the United States Food & Drug Administration in 1967 as an ovulatory stimulant, is an isomeric mixture of the citrate salts of cis-clomiphene (Z-clomiphene or 'zuclomiphene', (1-A)) and trans-clomiphene (E-clomiphene or 'enclomiphene', (1-B)) containing between 30% and 50% of the cis-isomer. Pure cis-isomer zuclomiphene, or (2-[4-[(Z)-2-chloro-1,2-diphenylethenyl]phenoxy]-N,N-diethylethanamine), in the form of the citrate salt, is currently under evaluation in clinical trials in the United States to treat hot flashes experienced by male patients with advanced prostate cancer undergoing androgen deprivation therapy (ADT).

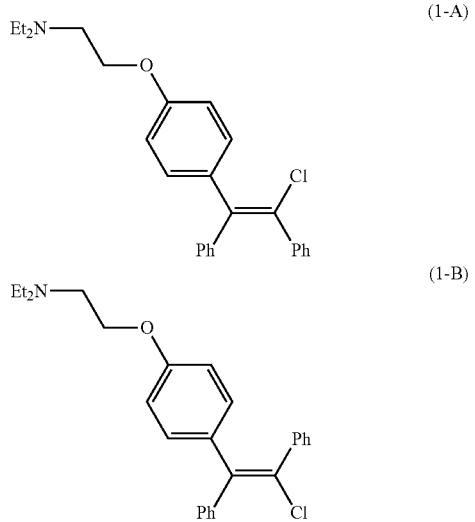

Until recently, interest in clomiphene isomers has largely focused on the E-isomer enclomiphene or mixtures thereof with zuclomiphene. Likewise, all reported synthetic methods to date, including for example Palopoli et al. *J. Med. Chem.* 1967, 10 (1), 84-6, WO 2014/031177 A1 and U.S. Pat. No. 9,428,442 B2 have afforded isomeric clomiphene mixtures which are typically comprised of 50-70% enclomiphene. Reported methods for the separation of zuclomiphene from enclomiphene in a typical mixture comprise fractional crystallization of zuclomiphene free form or a salt thereof.

In U.S. Pat. No. 9,428,442 B2, it is reported that a mixture of clomiphene isomers can be separated by treating the mixture with racemic binaphthyl hydrogen phosphate ('BPA') in methanol. This procedure was originally described in U.S. Pat. No. 3,848,030 A, however the isomeric configurations were wrongly assigned therein and examples 31 and 32 have since been reported to afford the E- and Z-isomers, respectively, rather than the reverse configuration. Applying the correction to the separation procedure described in U.S. Pat. No. 3,848,030 A, the E-isomer enclomiphene separates out as the BPA salt which is collected by filtration and subsequently converted to the corresponding citrate salt. The Z-isomer zuclomiphene is recovered from the filtrate by addition of ammonia and extraction of the resulting free base into ether solvent followed by treatment of the extracts with an ethanolic citric acid solution to afford solid zuclomiphene citrate having a melting point of 120-126° C.

In Dolginova et al. *Pharm. Chem. J.* 1984, 11, 758, a procedure for the isolation of zuclomiphene by fractional crystallization of a mixture of clomiphene isomers from petroleum ether and hexane is reported. The resulting zuclomiphene free base is treated with citric acid in isopropanol to afford crystalline zuclomiphene citrate having a melting point of 148-149° C.

Crystalline Forms I and VI of zuclomiphene citrate are described in FR3082842 having respective melting points, defined therein as the point at which the sample is fully in the liquid phase, of 136° C. and 140° C.

Different crystalline forms of the same compound may have different crystal packing, thermodynamic, spectroscopic, kinetic, surface and mechanical properties. For example, different crystalline forms may have different stability properties such that a particular crystalline form may be less sensitive to heat, relative humidity (RH) and/or light. Different crystalline forms of a compound may also be more susceptible to moisture uptake, resulting in a potential alteration of physical characteristics of the form such as flowability, density or compressibility, which can lead to problems during formulation/tabletting and/or to changes in dissolution rate of the formulated drug product.

For example, a particular crystalline form may provide more favourable compressibility and/or density properties, thereby providing more desirable characteristics for formulation and/or product manufacturing. Differences in stability between solid forms of a drug may result from changes in chemical reactivity, such as differential oxidation. Such properties may provide for more suitable product qualities, including a dosage form that is more resistant to discolouration when comprised of a specific crystalline form. Particular crystalline forms may also have different solubilities, thereby providing different pharmacokinetic parameters, which allow for specific crystalline forms to be used in order to achieve specific pharmacokinetic targets.

Although general approaches to crystalline form screening of active pharmaceutical ingredients are known, it is well established that the prediction of whether any given compound will exhibit polymorphism is not possible. Accordingly, it is not possible to extend generalities to the number and kinds of crystalline forms that can exist for zuclomiphene citrate, or to what methods will be suitable for the preparation of any given crystalline form. Furthermore, prediction of the properties of any unknown crystalline forms, and how they will differ from other crystalline forms of the same compound, remains elusive (Joel Bernstein, *Polymorphism in Molecular Crystals*, Oxford University Press, New York, 2002, page 9).

There exists a need for novel crystalline forms of zuclomiphene citrate having improved properties for use in providing drug products containing zuclomiphene citrate, and commercially amenable processes for their manufacture.

SUMMARY OF THE INVENTION

The present invention provides novel crystalline forms of zuclomiphene citrate that can be prepared by efficient and industrially compatible processes. Additionally, embodiments of the present invention exhibit stability when exposed to conditions of 40° C./75% RH.

Accordingly, in a first aspect of the present invention, there is provided a crystalline form of zuclomiphene citrate, APO-I, characterized by a PXRD diffractogram comprising peaks, expressed in degrees 2θ (±0.2°), at 8.8°, 9.6° and 11.7°. In a preferred embodiment of the first aspect, the PXRD diffractogram further comprises at least three peaks, expressed in degrees 2θ (±0.2°), selected from the group consisting of: 10.9°, 12.4°, 14.7°, 14.9°, 17.3°, 17.8°, 18.6°, 19.9°, 20.5°, 23.6°, and 25.4°. In a further preferred embodiment of the first aspect, the PXRD diffractogram further comprises peaks, expressed in degrees 2θ (±0.2°), at 10.9°, 12.4°, 14.7°, 14.9°, 17.3°, 17.8°, 18.6°, 19.9°, 20.5°, 23.6°, and 25.4°. Preferably, the crystalline form of the first aspect of the invention provides a PXRD diffractogram comprising peaks in substantially the same positions (±0.2° 2θ) as those shown in FIG. 1. In a further preferred embodiment of the first aspect, the crystalline form is characterized by a DSC thermogram comprising an endothermic peak with a peak onset at about 140° C. and a peak maximum at about 142° C. Preferably, the crystalline form of the first aspect is characterized by a DSC thermogram that is substantially the same in appearance as the DSC thermogram provided in FIG. 5.

In a second aspect of the present invention, there is provided a process for the preparation of a crystalline form of zuclomiphene citrate according to the first aspect of the invention, the process comprising exposing zuclomiphene citrate Form APO-II to water vapour at a suitable temperature for a suitable time.

In a preferred embodiment of the second aspect, exposing zuclomiphene citrate Form APO-II to water vapour comprises storing the zuclomiphene citrate Form APO-II in a closed chamber having a controlled relative humidity, preferably wherein the relative humidity is between approximately 40% RH and approximately 100% RH. In a further preferred embodiment of the second aspect, the suitable temperature is between approximately 30° C. and approximately 65° C.

In a third aspect of the present invention, there is provided a crystalline form of zuclomiphene citrate, APO-II, characterized by a PXRD diffractogram comprising peaks, expressed in degrees 2θ (±0.2°), at 8.3°, 8.7° and 15.2°. In a preferred embodiment of the third aspect, the PXRD diffractogram further comprises at least three peaks, expressed in degrees 2θ (±0.2°), selected from the group consisting of: 9.7°, 11.1°, 11.6°, 12.1°, 16.8°, 17.6°, 20.4° and 23.6°. In a further preferred embodiment of the third aspect, the PXRD diffractogram further comprises peaks, expressed in degrees 2θ (±0.2°), at 9.7°, 11.1°, 11.6°, 12.1°, 16.8°, 17.6°, 20.4° and 23.6°. Preferably, the crystalline form of the third aspect of the invention provides a PXRD diffractogram comprising peaks in substantially the same positions (±0.2° 2θ) as those shown in FIG. 2. In a further preferred embodiment of the third aspect, the crystalline form is characterized by a DSC thermogram comprising an endothermic peak with a peak onset at about 138° C. and a peak maximum at about 140° C. Preferably, the crystalline form of the third aspect is characterized by a DSC thermogram that is substantially the same in appearance as the DSC thermogram provided in FIG. 6.

In a fourth aspect of the present invention, there is provided a crystalline form of zuclomiphene citrate, APO-III, characterized by a PXRD diffractogram comprising peaks, expressed in degrees 2θ (±0.2°), at 8.7°, 9.8° and 10.5°. In a preferred embodiment of the fourth aspect, the PXRD diffractogram further comprises at least three peaks, expressed in degrees 2θ (±0.2°), selected from the group consisting of: 11.6°, 12.3°, 15.3°, 16.9°, 18.0°, 18.6°, 19.4°, 20.4°, 21.0° and 24.5°. In a further preferred embodiment of the fourth aspect, the PXRD diffractogram further comprises peaks, expressed in degrees 2θ (±0.2°), at 11.6°, 12.3°, 15.3°, 16.9°, 18.0°, 18.6°, 19.4°, 20.4°, 21.0° and 24.5°. Preferably, the crystalline form of the fourth aspect of the invention provides a PXRD diffractogram comprising peaks in substantially the same positions (±0.2° 2θ) as those shown in FIG. 3. In a further preferred embodiment of the fourth aspect, the crystalline form is characterized by a DSC thermogram comprising an endothermic peak with a peak onset at about 140° C. and a peak maximum at about 143° C. Preferably, the crystalline form of the fourth aspect is characterized by a DSC thermogram that is substantially the same in appearance as the DSC thermogram provided in FIG. 7.

In a fifth aspect of the present invention, there is provided a crystalline form of zuclomiphene citrate, APO-IV, characterized by a PXRD diffractogram comprising peaks, expressed in degrees 2θ (±0.2°), at 8.5°, 10.3° and 13.8°. In a preferred embodiment of the fifth aspect, the PXRD diffractogram further comprises at least three peaks, expressed in degrees 2θ (±0.2°), selected from the group consisting of: 9.5°, 11.3°, 12.5°, 13.1°, 14.4°, 15.5°, 17.1°, 18.1°, 18.8° and 19.7°. In a further preferred embodiment of the fifth aspect, the PXRD diffractogram further comprises peaks, expressed in degrees 2θ (±0.2°), at 9.5°, 11.3°, 12.5°, 13.1°, 14.4°, 15.5°, 17.1°, 18.1°, 18.8° and 19.7°. Preferably, the crystalline form of the fifth aspect of the invention provides a PXRD diffractogram comprising peaks in substantially the same positions (±0.2° 2θ) as those shown in FIG. 4. In a further preferred embodiment of the fifth aspect, the crystalline form is characterized by a DSC thermogram comprising an endothermic peak with a peak onset at about 144° C. and a peak maximum at about 146° C. Preferably, the crystalline form of the fifth aspect is characterized by a DSC thermogram that is substantially the same in appearance as the DSC thermogram provided in FIG. 8.

In a sixth aspect of the present invention, there is provided a pharmaceutical composition comprising a crystalline form of zuclomiphene citrate according to the first, third, fourth or fifth aspects of the invention, or zuclomiphene citrate prepared according to the process of the second aspect of the invention, and one or more pharmaceutically acceptable excipients. Preferably, the pharmaceutical composition is in the form of a solid oral dosage form. Most preferably, the pharmaceutical composition is a capsule or a tablet. Preferably, the pharmaceutical composition of the sixth aspect comprises 50 mg of the crystalline form of zuclomiphene citrate of the first, third, fourth or fifth aspects of the invention.

In a seventh aspect of the present invention, there is provided the use of a crystalline form of zuclomiphene citrate according to the first, third, fourth or fifth aspects of the invention, or zuclomiphene citrate prepared according to the process of the second aspect of the invention, or the pharmaceutical compositions of the sixth aspect of the invention, in the treatment of a disorder selected from the group consisting of osteoporosis, bone fractures, loss of bone mineral density (BMD) and hot flashes. In a preferred embodiment of the seventh aspect, the disorder is hot flashes. In a further preferred embodiment of the seventh aspect, the treatment comprises suppressing or inhibiting hot flashes in a male patient undergoing androgen deprivation therapy for the treatment of prostate cancer.

In an eighth aspect of the present invention, there is provided a process for the preparation of the crystalline form of the fifth aspect of the invention, comprising combining zuclomiphene free base and citric acid in a solvent and crystallizing the zuclomiphene citrate using a condition selected from the group consisting of: (1) combining the zuclomiphene free base and citric acid at a controlled rate; (2) combining the zuclomiphene free base and citric acid at an elevated temperature; and (3) maintaining the zuclomiphene citrate for a period of time. In a preferred embodiment of the eighth aspect, the solvent is an alkyl ester. In a further preferred embodiment of the eighth aspect, the process comprises condition (1), (2), and (3). In another preferred embodiment of the eighth aspect, the elevated temperature is a temperature in the range of about 50° C. to about 70° C. In another preferred embodiment of the eighth aspect, the period of time is in the range of about 16 hours to about 48 hours.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention are described, by way of example only, with reference to the attached Figures.

DESCRIPTION OF THE INVENTION

Figure 1:
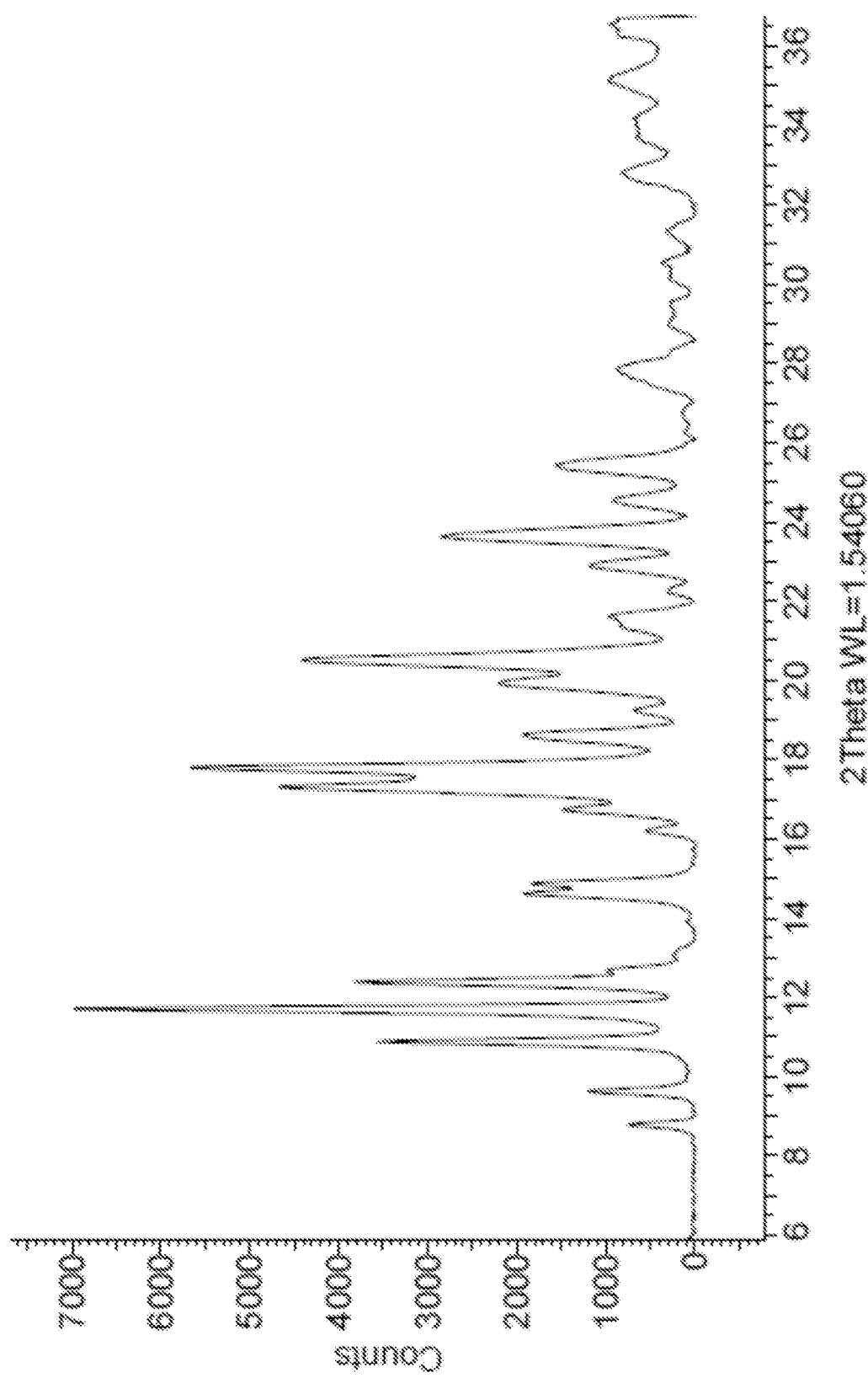
FIG. 1 is a representative PXRD diffractogram of zuclomiphene citrate Form APO-I as prepared in Example 2.

The present invention provides novel crystalline forms of zuclomiphene citrate.

The zuclomiphene citrate crystalline forms of the present invention exhibit differences in properties when compared to the known crystalline forms of zuclomiphene citrate. Properties that differ between the invention and known crystalline forms of zuclomiphene citrate include crystal packing properties such as molar volume, density and hygroscopicity; thermodynamic properties such as melting point and solubility; kinetic properties such as dissolution rate and chemical/polymorphic stability; surface properties such as crystal habit/particle morphology; and/or mechanical properties such as hardness, tensile strength, compactibility, tabletting, handling, flow, and blending.

Depending on the manner in which the crystalline forms of the present invention are prepared, and the methodology and instrument used for PXRD analysis, the intensity of a given peak observed in a PXRD diffractogram of a crystalline form may vary when compared to the same peak in the representative PXRD diffractogram provided in FIGS. 1 to 4. Thus, differences in relative peak intensities between peaks in a PXRD diffractogram for a given crystalline form may be observed when compared to the relative peak intensities of the peaks in the representative PXRD diffractogram of FIGS. 1 to 4. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractogram provided in FIGS. 1 to 4, it is understood that individual peak positions may vary between ±0.2° 2θ from the values observed in the representative PXRD diffractograms provided in FIGS. 1 to 4 for the crystalline form of the invention, or listed in Tables 1 to 4. Such variations are known and understood by a person of skill in the art, and any such variations do not depart from the invention disclosed herein.

Further, depending on the instrument used for X-ray analysis and its calibration, uniform offsets in the peak position of each peak in a PXRD diffractogram of greater that 0.2° 2θ may be observed when compared to the representative PXRD diffractograms provided in FIGS. 1 to 4. Thus, PXRD diffractograms of the crystalline form of the present invention may, in some circumstances, display the same relative peak positions as observed in the representative PXRD diffractograms provided in FIGS. 1 to 4, with the exception that each peak is offset in the same direction, and by approximately the same amount, such that the overall PXRD diffractogram is substantially the same in appearance as the PXRD diffractograms of FIGS. 1 to 4, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractograms of FIGS. 1 to 4.

Depending on the manner in which the crystalline forms are prepared, the methodology and instrument used for DSC analysis, it is understood that peaks corresponding with thermal events in a DSC thermogram may vary between ±2° C. from the values observed in the representative DSC thermograms provided in FIGS. 5 to 8 and described herein. Such variations are known and understood by a person of skill in the art, and any such variations do not depart from the invention disclosed herein.

As used herein, the term 'crystalline form' refers to a substance with a particular arrangement of molecular components in its crystal lattice, and which may be identified by physical characterization methods such as PXRD and/or DSC.

As used herein, the term "room temperature" refers to a temperature in the range of 20° C. to 25° C.

As used herein, the term "isomeric purity" refers to the amount of the subject zuclomiphene relative to the total amount of enclomiphene and zuclomiphene, expressed as a percentage.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

In one embodiment of the present invention, there is provided a new crystalline form of zuclomiphene citrate, zuclomiphene citrate Form APO-I. Preferably, Form APO-I is unsolvated. More preferably, Form APO-I is anhydrous and unsolvated.

Zuclomiphene citrate Form APO-1 can be characterized by a PXRD diffractogram comprising, among other peaks, characteristic peaks, expressed in degrees 2θ (±0.2°), at 8.8°, 9.6° and 11.7°. Preferably, the PXRD diffractogram further comprises at least three peaks, expressed in degrees 2θ (±0.2°), selected from the group consisting of 10.9°, 12.4°, 14.7°, 14.9°, 17.3°, 17.8°, 18.6°, 19.9°, 20.5°, 23.6° and 25.4°. More preferably, the PXRD diffractogram further comprises peaks, expressed in degrees 2θ (±) 0.2°, at 10.9°, 12.4°, 14.7°, 14.9°, 17.3°, 17.8°, 18.6°, 19.9°, 20.5°, 23.6° and 25.4°. PXRD studies of capped and uncapped samples of zuclomiphene citrate Form APO-1 maintained in a 40° C./75% RH stability chamber for at least 4 weeks showed that no change in the crystalline form occurred.

An illustrative PXRD diffractogram of zuclomiphene citrate Form APO-1, as prepared in Example 2, is shown in FIG. 1. A peak listing, comprising representative peaks from the PXRD diffractogram in FIG. 1, and their relative intensities, is provided in Table 1. Although illustrative of the PXRD diffractogram that is provided for the zuclomiphene citrate Form APO-1 of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of zuclomiphene citrate Form APO-I from Figure 1

| Angle (2θ) | Relative intensity (%) |
|---|---|
| 8.80 | 10.6 |
| 9.64 | 17.1 |
| 10.89 | 50.9 |
| 11.71 | 100.0 |
| 12.39 | 54.7 |
| 14.67 | 25.4 |
| 14.88 | 26.3 |
| 17.31 | 67.0 |
| 17.81 | 81.2 |
| 18.64 | 27.7 |
| 19.92 | 31.6 |

TABLE 1-continued

Relative peak intensities of zuclomiphene citrate Form APO-I from Figure 1

| Angle (2θ) | Relative intensity (%) |
|---|---|
| 20.51 | 63.4 |
| 22.89 | 16.9 |
| 23.63 | 40.9 |
| 24.53 | 13.3 |
| 25.44 | 22.5 |

Figure 5:
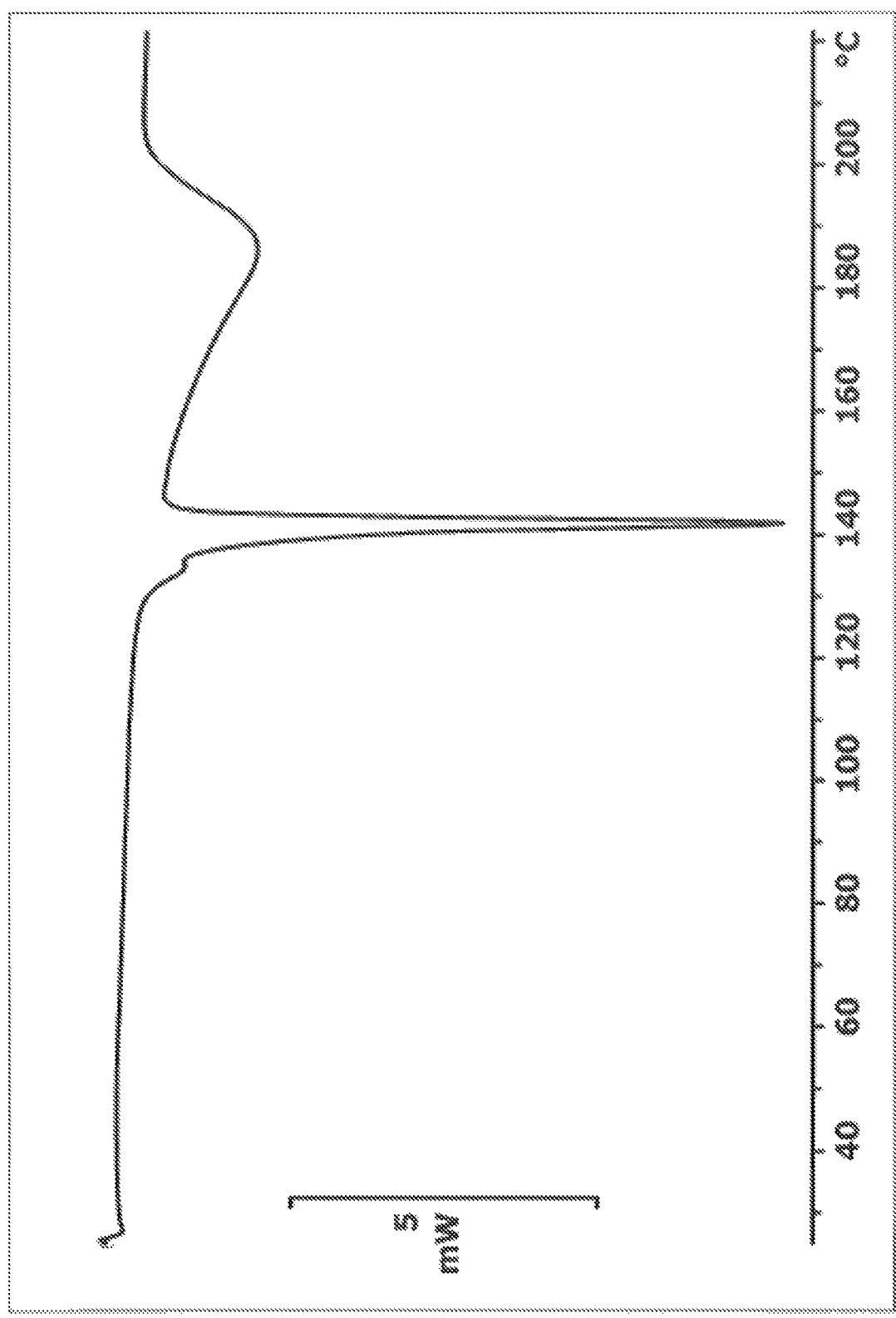
FIG. 5 is a representative DSC thermogram of zuclomiphene citrate Form APO-I as prepared in Example 2.

An illustrative DSC thermogram of zuclomiphene citrate Form APO-I is shown in FIG. 5. The DSC thermogram may be further characterized by an endothermic peak with a peak onset at about 140° C. and a peak maximum at about 142° C.

Zuclomiphene citrate Form APO-I can be prepared by exposing zuclomiphene citrate Form APO-II to water vapour at a suitable temperature for a suitable time.

Exposing zuclomiphene citrate Form APO-II to water vapour may comprise storing the zuclomiphene citrate Form APO-II in a closed chamber having a controlled relative humidity ('RH'). Preferably, the relative humidity is between approximately 40% RH and approximately 100% RH, most preferably the relative humidity is between approximately 80% RH and approximately 100% RH. The suitable temperature is preferably elevated, and is preferably between approximately 30° C. and approximately 65° C. The suitable time will depend on the temperature and relative humidity. Generally, higher temperatures and higher levels of relative humidity will accelerate the conversion of Form APO-II to Form APO-I.

In a second embodiment of the present invention, there is provided a new crystalline form of zuclomiphene citrate, zuclomiphene citrate Form APO-II. Preferably, Form APO-II is unsolvated. More preferably, Form APO-II is anhydrous and unsolvated.

Zuclomiphene citrate Form APO-II can be characterized by a PXRD diffractogram comprising, among other peaks, characteristic peaks, expressed in degrees 2θ (±0.2°), at 8.3°, 8.7° and 15.2°. Preferably, the PXRD diffractogram further comprises at least three peaks, expressed in degrees 2θ (±0.2°), selected from the group consisting of 9.7°, 11.1°, 11.6°, 12.1°, 16.8°, 17.6°, 20.4° and 23.6°. More preferably, the PXRD diffractogram further comprises peaks, expressed in degrees 2θ (±0.2°), at 9.7°, 11.1°, 11.6°, 12.1°, 16.8°, 17.6°, 20.4° and 23.6°.

Figure 2:
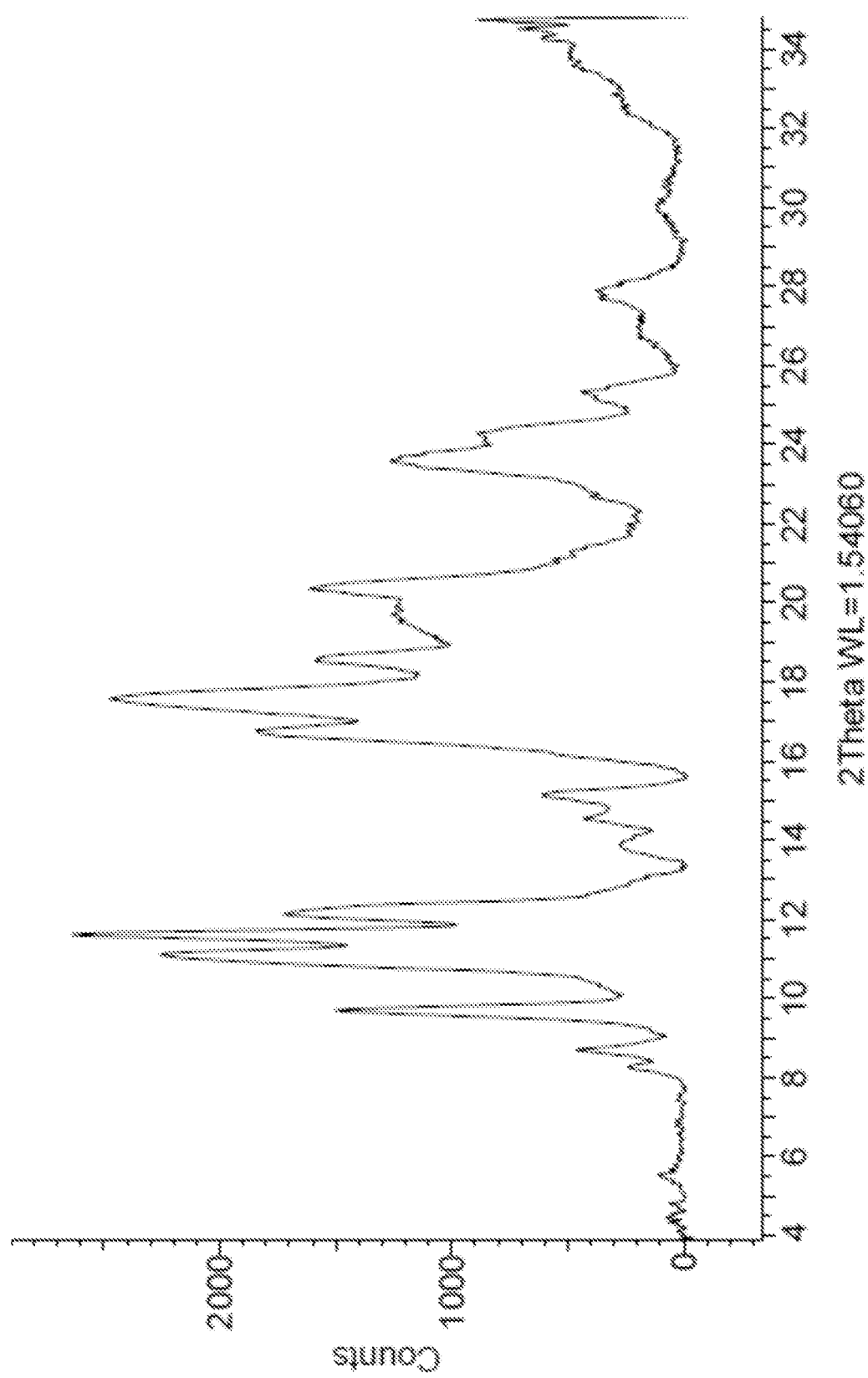
FIG. 2 is a representative PXRD diffractogram of zuclomiphene citrate Form APO-II as prepared in Example 1.

An illustrative PXRD diffractogram of zuclomiphene citrate Form APO-II, as prepared in Example 1, is shown in FIG. 2. A peak listing, comprising representative peaks from the PXRD diffractogram in FIG. 2, and their relative intensities, is provided in Table 2. Although illustrative of the PXRD diffractogram that is provided for the zuclomiphene citrate Form APO-II of the present invention, the relative intensities of the peaks are variable. Thus, depending on a particular sample, the prominence or relative intensity of the peaks observed may differ from those in the illustrative PXRD diffractogram and peak listing.

TABLE 2

Relative peak intensities of zuclomiphene citrate Form APO-II from Figure 2

| Angle (2θ) | Relative intensity (%) |
|---|---|
| 8.28 | 9.1 |
| 8.71 | 17.6 |

TABLE 2-continued

Relative peak intensities of zuclomiphene
citrate Form APO-II from Figure 2

| Angle (2θ) | Relative intensity (%) |
|---|---|
| 9.70 | 57.0 |
| 11.11 | 85.5 |
| 11.61 | 100.0 |
| 12.14 | 65.5 |
| 13.90 | 10.4 |
| 15.15 | 23.1 |
| 16.77 | 69.9 |
| 17.58 | 93.9 |
| 18.55 | 60.2 |
| 20.36 | 61.3 |
| 23.60 | 47.9 |

Figure 6:
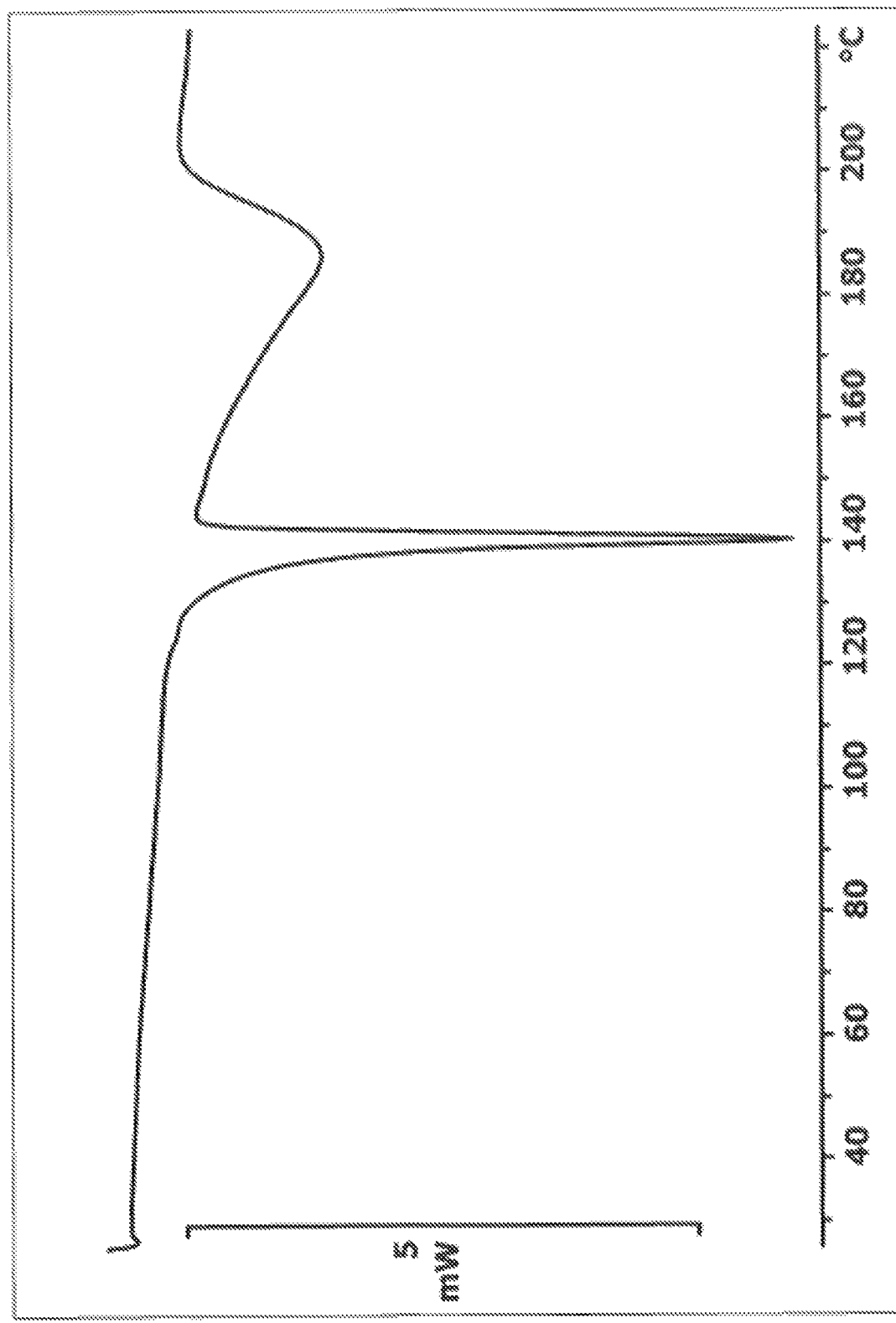
FIG. 6 is a representative DSC thermogram of zuclomiphene citrate Form APO-II as prepared in Example 1.

An illustrative DSC thermogram of zuclomiphene citrate Form APO-II is shown in FIG. 6. The DSC thermogram may be further characterized by an endothermic peak with a peak onset at about 138° C. and a peak maximum at about 140° C.

In a third embodiment of the present invention, there is provided a new crystalline form of zuclomiphene citrate, zuclomiphene citrate Form APO-III. Preferably, Form APO-III is unsolvated. More preferably, Form APO-III is anhydrous and unsolvated.

Zuclomiphene citrate Form APO-III can be characterized by a PXRD diffractogram comprising, among other peaks, characteristic peaks, expressed in degrees 2θ (±0.2°), at 8.7°, 9.8° and 10.5°. Preferably, the PXRD diffractogram further comprises at least three peaks, expressed in degrees 2θ (±0.2°), selected from the group consisting of 11.6°, 12.3°, 15.3°, 16.9°, 18.0°, 18.6°, 19.4°, 20.4°, 21.0° and 24.5°. More preferably, the PXRD diffractogram further comprises peaks, expressed in degrees 2θ (±0.2°), at 11.6°, 12.3°, 15.3°, 16.9°, 18.0°, 18.6°, 19.4°, 20.4°, 21.0° and 24.5°. PXRD studies of capped and uncapped samples of zuclomiphene citrate Form APO-III maintained in a 40° C./75% RH stability chamber for at least 8 weeks showed that no change in the crystalline form occurred.

Figure 3:
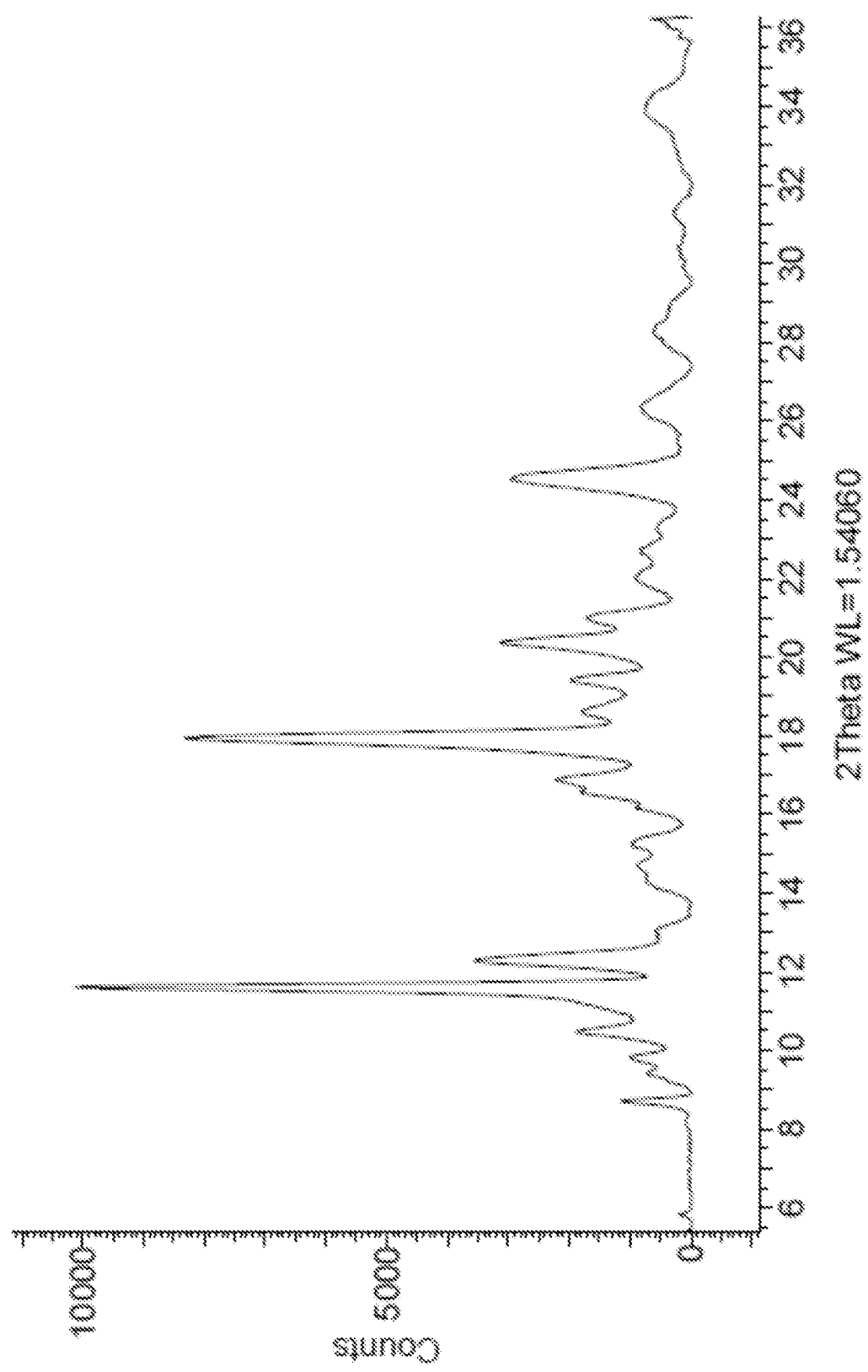
FIG. 3 is a representative PXRD diffractogram of zuclomiphene citrate Form APO-III as prepared in Example 3.

An illustrative PXRD diffractogram of zuclomiphene citrate Form APO-III, as prepared in Example 3, is shown in FIG. 3. A peak listing, comprising representative peaks from the PXRD diffractogram in FIG. 3, and their relative intensities, is provided in Table 3. Although illustrative of the PXRD diffractogram that is provided for the zuclomiphene citrate Form APO-III of the present invention, the relative intensities of the peaks are variable. Thus, depending on a particular sample, the prominence or relative intensity of the peaks observed may differ from those in the illustrative PXRD diffractogram and peak listing.

TABLE 3

Relative peak intensities of zuclomiphene
citrate Form APO-III from Figure 3

| Angle (2θ) | Relative intensity (%) |
|---|---|
| 8.72 | 11.3 |
| 9.83 | 9.9 |
| 10.48 | 18.5 |
| 11.61 | 100.0 |
| 12.30 | 35.2 |
| 15.27 | 9.6 |
| 16.89 | 22.0 |
| 17.95 | 82.3 |
| 18.61 | 17.8 |
| 19.42 | 19.5 |

TABLE 3-continued

Relative peak intensities of zuclomiphene
citrate Form APO-III from Figure 3

| Angle (2θ) | Relative intensity (%) |
|---|---|
| 20.37 | 31.0 |
| 21.00 | 17.0 |
| 24.52 | 29.3 |

Figure 7:
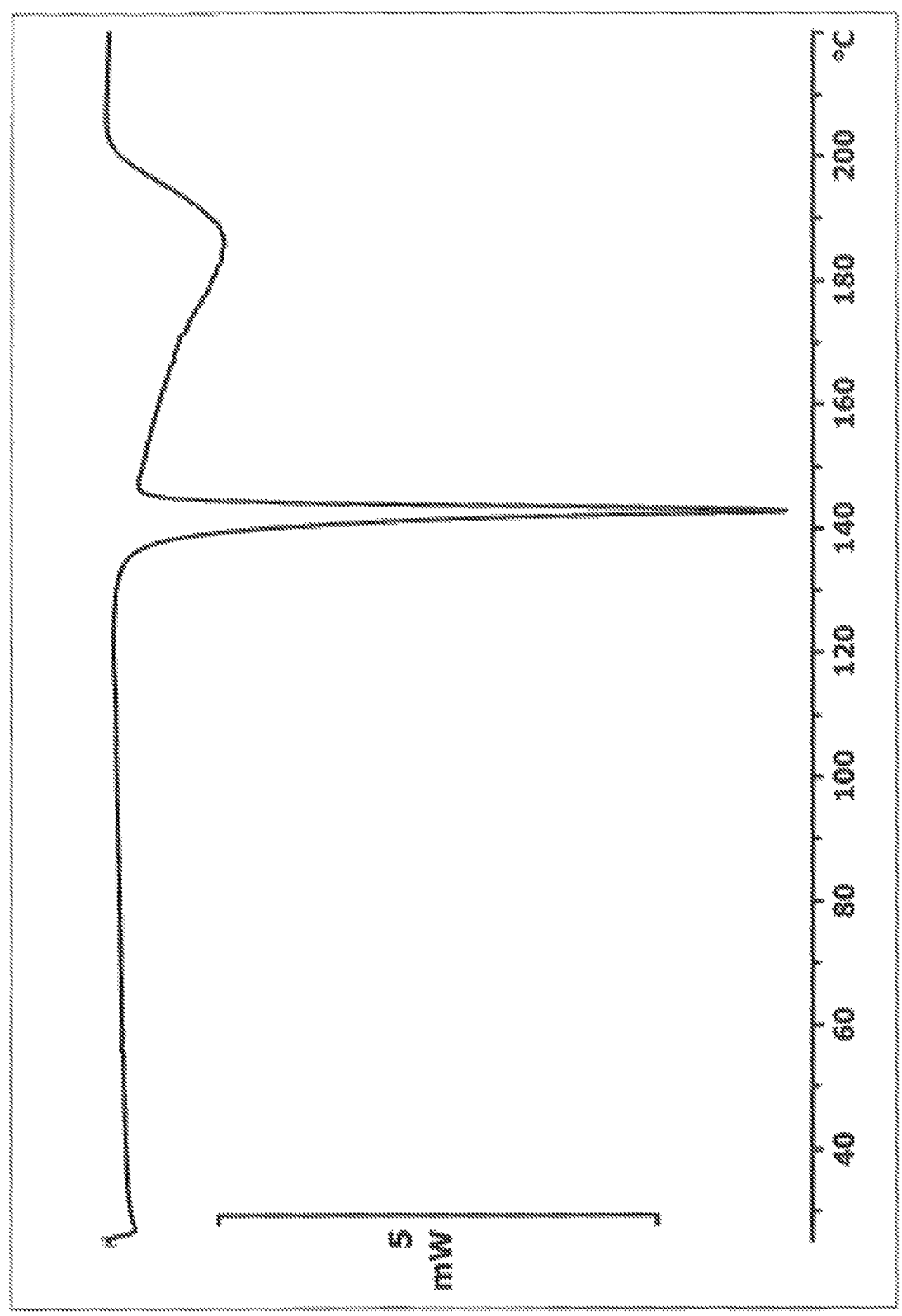
FIG. 7 is a representative DSC thermogram of zuclomiphene citrate Form APO-III as prepared in Example 3.

An illustrative DSC thermogram of zuclomiphene citrate Form APO-III is shown in FIG. 7. The DSC thermogram may be further characterized by an endothermic peak with a peak onset at about 140° C. and a peak maximum at about 143° C.

Zuclomiphene citrate Form APO-III can be prepared by adding a solution of citric acid in an alcohol solvent, preferably methanol or ethanol, to a solution of zuclomiphene free base in dimethyl carbonate or a ketone solvent. Preferably, the solution of zuclomiphene free base is heated to an elevated temperature prior to addition of the citric acid solution, preferably in the range of 40° C. to 60° C. Following salt formation, the resulting mixture is preferably cooled prior to isolation of the solid by filtration and drying, if necessary.

In a fourth embodiment of the present invention, there is provided a new crystalline form of zuclomiphene citrate, zuclomiphene citrate Form APO-IV. Preferably, Form APO-IV is unsolvated. More preferably, Form APO-IV is anhydrous and unsolvated.

Zuclomiphene citrate Form APO-IV can be characterized by a PXRD diffractogram comprising, among other peaks, characteristic peaks, expressed in degrees 2θ (±0.2°), at 8.5°, 10.3° and 13.8°. Preferably, the PXRD diffractogram further comprises at least three peaks, expressed in degrees 2θ (±0.2°), selected from the group consisting of 9.5°, 11.3°, 12.5°, 13.1°, 14.4°, 15.5°, 17.1°, 18.1°, 18.8° and 19.7°. More preferably, the PXRD diffractogram further comprises peaks, expressed in degrees 2θ (±) 0.2°, at 9.5°, 11.3°, 12.5°, 13.1°, 14.4°, 15.5°, 17.1°, 18.1°, 18.8° and 19.7°. PXRD studies of capped and uncapped samples of zuclomiphene citrate Form APO-IV maintained in a 40° C./75% RH stability chamber for at least 8 weeks showed that no change in the crystalline form occurred.

Figure 4:
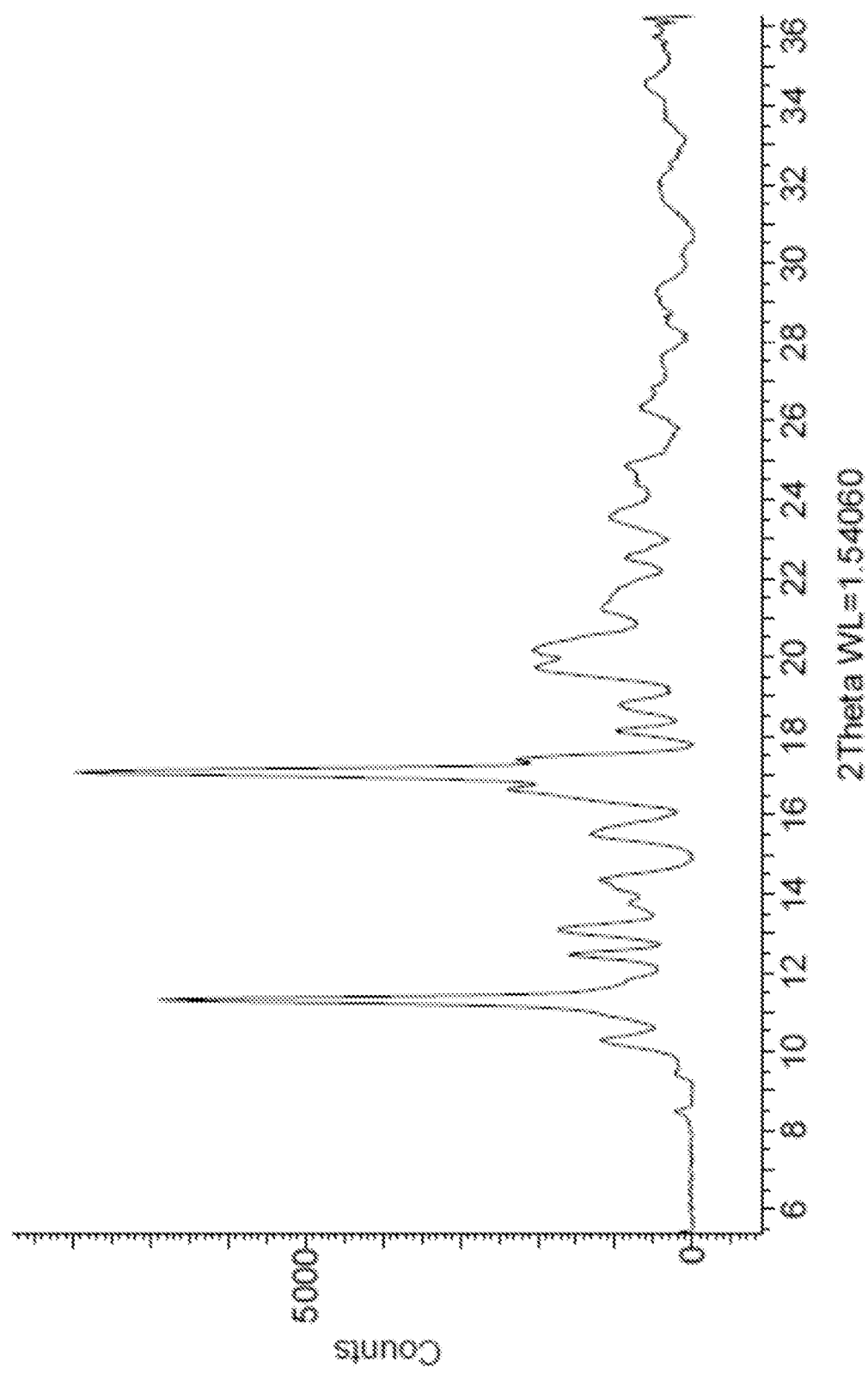
FIG. 4 is a representative PXRD diffractogram of zuclomiphene citrate Form APO-IV as prepared in Example 5.

An illustrative PXRD diffractogram of zuclomiphene citrate Form APO-IV, as prepared in Example 5, is shown in FIG. 4. A peak listing, comprising representative peaks from the PXRD diffractogram in FIG. 4, and their relative intensities, is provided in Table 4. Although illustrative of the PXRD diffractogram that is provided for the zuclomiphene citrate Form APO-IV of the present invention, the relative intensities of the peaks are variable. Thus, depending on a particular sample, the prominence or relative intensity of the peaks observed may differ from those in the illustrative PXRD diffractogram and peak listing.

TABLE 4

Relative peak intensities of zuclomiphene
citrate Form APO-IV from Figure 4

| Angle (2θ) | Relative intensity (%) |
|---|---|
| 8.49 | 2.9 |
| 9.47 | 2.7 |
| 10.29 | 14.8 |
| 11.32 | 86.2 |
| 12.46 | 20.0 |

TABLE 4-continued

Relative peak intensities of zuclomiphene citrate Form APO-IV from Figure 4

| Angle (2θ) | Relative intensity (%) |
|---|---|
| 13.09 | 21.7 |
| 13.77 | 10.3 |
| 14.35 | 15.0 |
| 15.52 | 16.6 |
| 16.65 | 29.9 |
| 17.08 | 100.0 |
| 17.37 | 27.5 |
| 18.13 | 12.3 |
| 18.80 | 11.9 |
| 19.74 | 25.5 |
| 20.18 | 25.9 |
| 22.52 | 11.0 |
| 23.56 | 13.3 |

Figure 8:
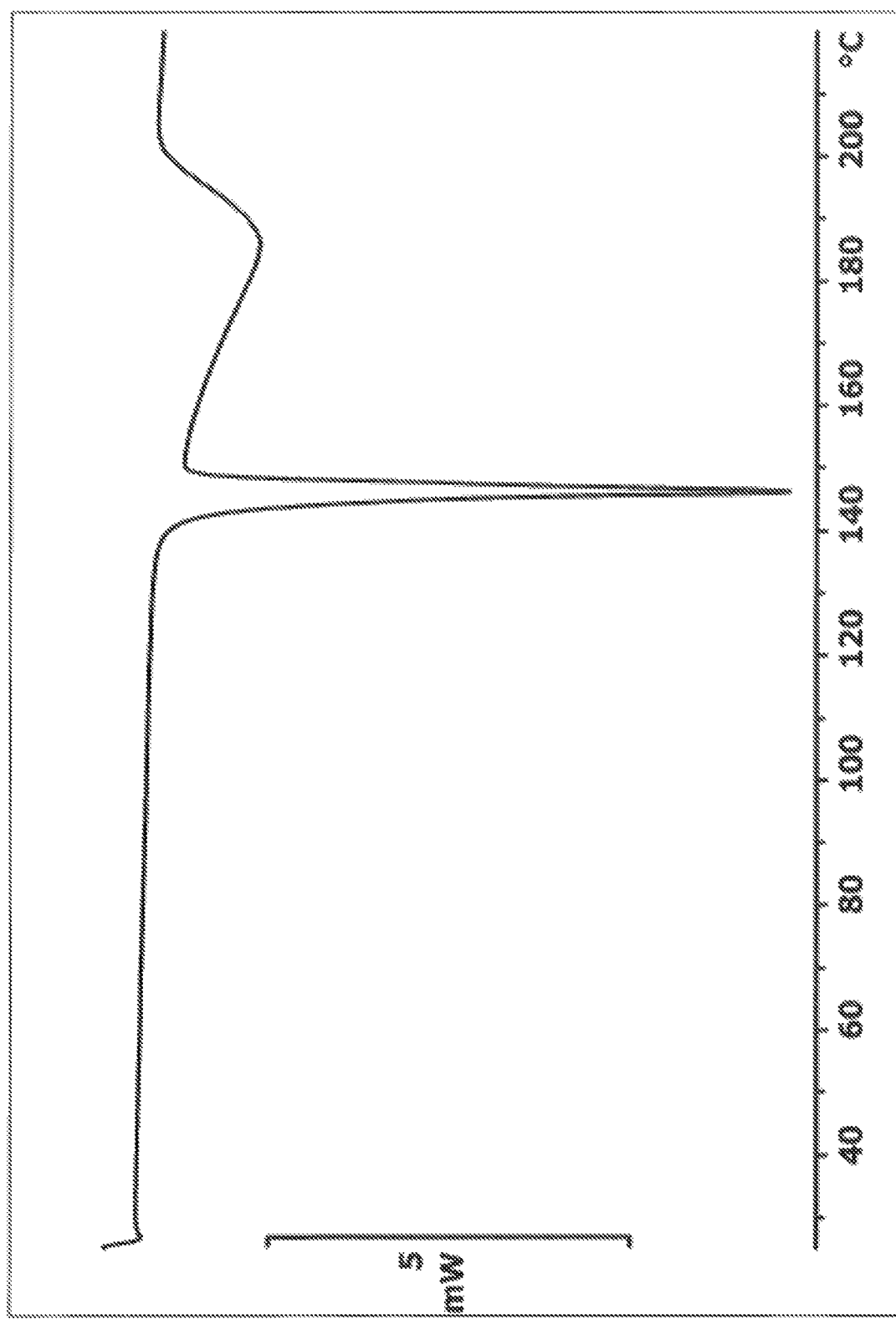
FIG. 8 is a representative DSC thermogram of zuclomiphene citrate Form APO-IV as prepared in Example 5.

An illustrative DSC thermogram of zuclomiphene citrate Form APO-IV is shown in FIG. 8. The DSC thermogram may be further characterized by an endothermic peak with a peak onset at about 144° C. and a peak maximum at about 146° C.

Zuclomiphene citrate Form APO-IV is thermodynamically stable. As such, zuclomiphene citrate Form APO-IV can be prepared, for example, by inducing crystallization of the salt under conditions that favour a thermodynamically stable form. Crystallization factors which favour a thermodynamically stable form are those which favour 'slow' crystallization including, for example, controlled rate of contact of zuclomiphene free base with citric acid; elevated temperature of crystallization, preferably in the range of at least about 50° C. and at most about 70° C.; extended aging of crystals at elevated temperature, preferably at least about 16 hours and at most about 4 days, preferably in the range of about 50° C. to about 70° C.; no precipitant; and/or combinations thereof. Zuclomiphene citrate Form APO-IV can be prepared by gradual addition of a solution of citric acid in a suitable solvent, preferably an alcohol or ketone solvent such as methanol or acetone, to a solution of zuclomiphene free base in a suitable solvent, preferably an alcohol solvent such as 2-methyl-1-propanol or 1-butanol, more preferably an ester solvent, such as ethyl acetate. Preferably, the solution of zuclomiphene free base is heated to an elevated temperature prior to addition of the citric acid solution, preferably in the range of about 50° C. to about 70° C. Following addition, the resulting mixture is preferably charged with Form APO-IV seeds and maintained at elevated temperature for a time ('aged'), preferably in the range of about 16 hours to about 4 days, more preferably in the range of about 16 hours to about 48 hours. Following aging, the resulting mixture is preferably cooled to a temperature in the range of about 0° C. to about 35° C., most preferably room temperature, prior to isolation of the solid by filtration and drying, if necessary. Drying can be conducted in vacuo, preferably at a temperature in the range of about 50° C. to about 70° C., preferably for about 18 hours to about 3 days.

In a further embodiment of the invention, there is provided a pharmaceutical composition comprising zuclomiphene citrate Form APO-I, zuclomiphene citrate Form APO-II, zuclomiphene citrate Form APO-III, or zuclomiphene citrate Form APO-IV, with one or more pharmaceutically acceptable excipients. Preferably, the pharmaceutical composition is a solid dosage form suitable for oral administration, such as a capsule, tablet, pill, powder or granulate. Most preferably, the pharmaceutical composition is a tablet or a capsule. Preferably, the pharmaceutical composition provides a dose of zuclomiphene citrate that is equivalent to the 1 to 80 mg of zuclomiphene citrate that is described as a dosage range in U.S. Pat. No. 9,913,815 B2. More preferably, the pharmaceutical composition provides a dose of zuclomiphene citrate that is equivalent to the 50 mg of zuclomiphene citrate that was demonstrated in interim Phase 2 clinical trial results to provide a statistically significant decrease in moderate to severe hot flashes from baseline (Veru Inc. "*Veru Announces Positive Top-Line Interim Data from Phase 2 Clinical Trial of Zuclomiphene to Treat Hot Flashes in Men with Prostate Cancer on Androgen Deprivation Therapy.*" Veru Inc. press release, Jan. 12, 2020. On the Veru Inc. website. https://verupharma.com/news/, accessed Jan. 16, 2020).

Suitable pharmaceutically acceptable excipients are preferably inert with respect to the crystalline forms of zuclomiphene citrate of the present invention, and may include, for example, one or more excipients selected from binders such as lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatine, polyvinylpyrrolidone (PVP) and sodium alginate; fillers or diluents such as lactose, sugar, starches, modified starches, mannitol, sorbitol, inorganic salts, cellulose derivatives (e.g., microcrystalline cellulose, cellulose), calcium sulphate, xylitol and lactitol; disintegrants such as croscarmellose sodium, crospovidone, polyvinylpyrrolidone, sodium starch glycollate, corn starch, microcrystalline cellulose, hydroxypropyl methylcellulose and hydroxypropyl cellulose; lubricants such as magnesium stearate, magnesium lauryl stearate, sodium stearyl fumarate, stearic acid, calcium stearate, zinc stearate, potassium benzoate, sodium benzoate, myristic acid, palmitic acid, mineral oil, hydrogenated castor oil, medium-chain triglycerides, poloxamer, polyethylene glycol and talc; and dispersants or solubility enhancing agents, such cyclodextrins, glyceryl monostearate, hypromellose, meglumine, Poloxamer, polyoxyethylene castor oil derivatives, polyoxyethylene stearates, polyoxylglycerides, povidone, and stearic acid. Other excipients including preservatives, stabilisers, anti-oxidants, silica flow conditioners, antiadherents or glidants may be added as required. Other suitable excipients and the preparation of solid oral dosage forms are well known to person of skill in the art, and is described generally, for example, in *Remington The Science and Practice of Pharmacy* $21^{st}$ Edition (Lippincott Williams & Wilkins: Philadelphia; 2006; Chapter 45).

Optionally, when the pharmaceutical compositions are solid dosage forms, the solid dosage forms may be prepared with coatings, such as enteric coatings and extended release coatings, using standard pharmaceutical coatings. Such coatings, and their application, are well known to persons skilled in the art, and are described, for example, in *Remington The Science and Practice of Pharmacy* $21^{st}$ Edition (Lippincott Williams & Wilkins: Philadelphia; 2006; Chapter 46).

EXAMPLES

The following non-limiting examples are illustrative of some of the aspects and embodiments of the invention described herein. The zuclomiphene free base used as a starting material in Examples 1-3 and 5 showed an isomeric purity by $^1$H NMR analysis of at least about 98%.

PXRD Analysis:

PXRD diffractograms were recorded on a Bruker D8 Discover powder X-ray diffractometer (Bruker-AXS, Karlsruhe, Germany). The generator was a Micro-focus X-ray source (IMSTube: Cu tube with 1.54060 Å) with a voltage of 50 kV and current of 1.00 mA, using a divergence slit of 0.3 mm and collimator of 0.3 mm. For each sample, one frame was collected using a still scan with a Pilatus 3R-100 kA detector at the distance of 154.72 mm from the sample. Raw data were evaluated using the program EVA (Bruker-AXS, Karlsruhe, Germany).

Differential Scanning calorimetry Analysis:

DSC thermogram was collected on a Mettler-Toledo 821e instrument. A sample (1.4 to 3 mg) was weighed into a 40 μL aluminum pan and was crimped closed with an aluminum lid having a 50 μm perforation. The sample was analyzed under a flow of nitrogen (50±5 mL/min) at a scan rate of 10° C./minute between 25° C. and 360° C.

Example 1: Preparation of Zuclomiphene Citrate Form APO-II

To a suspension of zuclomiphene free base (153 mg) in tert-butyl methyl ether (3.5 mL) heated to 50° C. was added, in one portion, an aliquot (150 μL) of a solution of citric acid (2.09 g) in methanol (3.0 mL). Heating was continued for approximately one hour, after which the resulting thick suspension was stirred at room temperature for approximately 16 hours. The precipitated solids were collected by vacuum filtration, washed with tert-butyl methyl ether (2×1.0 mL) and dried in vacuo at room temperature to afford zuclomiphene citrate Form APO-II as a white solid (218 mg, 96% yield). $^1$H NMR analysis of the solid (DMSO-d$_6$, 300 MHz) indicated a molar ratio of zuclomiphene:citric acid of approximately 1:1 and no incorporation of solvent. The PXRD diffractogram and DSC thermogram of a sample prepared by this method are shown in FIG. 2 and FIG. 6, respectively.

Example 2: Preparation of Zuclomiphene Citrate Form APO-I

Solid zuclomiphene citrate Form APO-II as prepared in Example 1 was subjected to heating at 60° C. and 100% relative humidity for 70 hours to afford zuclomiphene citrate Form APO-I. $^1$H NMR analysis of the solid (DMSO-d$_6$, 300 MHz) indicated a molar ratio of zuclomiphene:citric acid of approximately 1:1. Karl Fischer (KF) analysis of the sample showed water content of 0.1367 wt %, which is consistent with an anhydrous form. The PXRD diffractogram and DSC thermogram of a sample prepared by this method are shown in FIG. 1 and FIG. 5, respectively.

Example 3: Preparation of Zuclomiphene Citrate Form APO-III

Zuclomiphene free base (1.84 g) was dissolved in acetone (20.0 mL) and the resulting solution was heated to 45° C. A solution of citric acid (909 mg) in ethanol (3.0 mL) was added in one portion, and the heat was turned off. Precipitation occurred within minutes, after which the suspension was cooled in an ice water bath for approximately 10 minutes. The solids were collected by vacuum filtration, washed with acetone (3×2.5 mL) and dried in vacuo at room temperature to afford zuclomiphene citrate Form APO-III as a white solid (2.45 g, 90% yield). $^1$H NMR analysis of the solid (DMSO-d$_6$, 300 MHz) indicated a molar ratio of zuclomiphene:citric acid of approximately 1:1 and no incorporation of solvent. The PXRD diffractogram and DSC thermogram of a sample prepared by this method are shown in FIG. 3 and FIG. 7, respectively.

Example 4: Preparation of Zuclomiphene Citrate Form APO-III

A solution of zuclomiphene free base (8.2 g, isomeric HPLC purity 99.5%) in ethyl acetate (150 mL) was heated to 45-50° C. A solution of citric acid (3.7 g) in acetone (23 mL) was slowly added to the solution at 45-50° C. over approximately one hour to afford a uniform, stirrable suspension. After maintaining the suspension at 45-50° C. for approximately two hours, the mixture was stirred at room temperature for approximately 16 hours. The suspension was then further cooled to 0-5° C. and stirred for four hours. The suspension was filtered, and the filter cake was washed with cold ethyl acetate (2×10 mL). The damp solid was dried in vacuo at 55-60° C. for approximately 18 hours to afford zuclomiphene citrate Form APO-III as a white solid (11.5 g, 95.2% yield, isomeric HPLC purity 99.5%).

Example 5: Preparation of Zuclomiphene Citrate Form APO-IV

Zuclomiphene free base (150 mg) was dissolved in 1-butanol (3.5 mL) and the resulting solution was heated to 50° C. An aliquot (150 μL) of a solution of citric acid (2.03 g) in methanol (3.0 mL) was added in one portion, and the heating was continued for approximately one hour. The resulting suspension was stirred at room temperature for approximately 16 hours, after which the solids were collected by vacuum filtration, washed with 1-butanol (2×0.5 mL) and dried under vacuum at room temperature to afford zuclomiphene citrate Form APO-IV as a white solid (190 mg, 86% yield). $^1$H NMR analysis of the solid (DMSO-d$_6$, 300 MHz) indicated a molar ratio of zuclomiphene:citric acid of approximately 1:1 and no incorporation of solvent. The PXRD diffractogram and DSC thermogram of a sample prepared by this method are shown in FIG. 4 and FIG. 8, respectively.

Example 6: Preparation of Zuclomiphene Citrate Form APO-IV

A solution of zuclomiphene free base (8.2 g, isomeric HPLC purity 99.0%) in ethyl acetate (150 mL) was heated to 50-55° C. A solution of citric acid (3.7 g) in acetone (35 mL) was slowly added to the solution at 50-55° C. over approximately two hours to afford a uniform, stirrable suspension. After the addition of zuclomiphene citrate Form APO-IV seeds, the suspension was maintained at 50-55° C. for approximately 25 hours. The suspension was then further cooled to room temperature over approximately 1 hour. The suspension was filtered, and the filter cake was washed with acetone (2×10 mL). The damp solid was dried in vacuo at 55-60° C. for approximately 18 hours to afford zuclomiphene citrate Form APO-IV as a white solid (10.7 g, 89% yield, isomeric HPLC purity 99.2%).

What is claimed is:

1. A crystalline form of zuclomiphene citrate, characterized by a PXRD diffractogram comprising peaks, expressed in degrees 2θ (±0.2°), at 8.8°, 9.6° and 11.7°.

2. The crystalline form of claim 1, further comprising at least three peaks, expressed in degrees 2θ (±0.2°), selected from the group consisting of: 10.9°, 12.4°, 14.7°, 14.9°, 17.3°, 17.8°, 18.6°, 19.9°, 20.5°, 23.6° and 25.4°.

3. The crystalline form of claim 1, characterized by a DSC thermogram comprising an endothermic peak with a peak onset at about 140° C. and a peak maximum at about 142° C.

4. A crystalline form of zuclomiphene citrate, characterized by a PXRD diffractogram comprising peaks, expressed in degrees 2θ (±0.2°), at 8.3°, 8.7° and 15.2°.

5. The crystalline form of claim 4, further comprising at least three peaks, expressed in degrees 2θ (±0.2°), selected from the group consisting of: 9.7°, 11.1°, 11.6°, 12.1°, 16.8°, 17.6°, 20.4° and 23.6°.

6. The crystalline form of claim 4, characterized by a DSC thermogram comprising an endothermic peak with a peak onset at about 138° C. and a peak maximum at about 140° C.

7. A crystalline form of zuclomiphene citrate, characterized by a PXRD diffractogram comprising peaks, expressed in degrees 2θ (±0.2°), at 8.7°, 9.8° and 10.5°.

8. The crystalline form of claim 7, further comprising at least three peaks, expressed in degrees 2θ (±0.2°), selected from the group consisting of: 11.6°, 12.3°, 15.3°, 16.9°, 18.0°, 18.6°, 19.4°, 20.4°, 21.0° and 24.5°.

9. The crystalline form of claim 7, further comprising peaks in the PXRD diffractogram, expressed in degrees 2θ (±0.2°), at 11.6°, 12.3°, 15.3°, 16.9°, 18.0°, 18.6°, 19.4°, 20.4°, 21.0° and 24.5°.

10. The crystalline form of claim 7, characterized by a DSC thermogram comprising an endothermic peak with a peak onset at about 140° C. and a peak maximum at about 143° C.

11. A crystalline form of zuclomiphene citrate, characterized by a PXRD diffractogram comprising peaks, expressed in degrees 2θ (±0.2°), at 8.5°, 10.3° and 13.8°.

12. The crystalline form of claim 11, further comprising at least three peaks, expressed in degrees 2θ (±0.2°), selected from the group consisting of: 9.5°, 11.3°, 12.5°, 13.1°, 14.4°, 15.5°, 17.1°, 18.1°, 18.8° and 19.7°.

13. The crystalline form of claim 11, further comprising peaks in the PXRD diffractogram, expressed in degrees 2θ (±0.2°), at 9.5°, 11.3°, 12.5°, 13.1°, 14.4°, 15.5°, 17.1°, 18.1°, 18.8° and 19.7°.

14. The crystalline form of claim 11, providing a PXRD diffractogram comprising peaks in substantially the same positions (±0.2° 2θ) as those shown in FIG. 4.

15. The crystalline form of claim 11, characterized by a DSC thermogram comprising an endothermic peak with a peak onset at about 144° C. and a peak maximum at about 146° C.

16. The crystalline form of claim 15, characterized by a DSC thermogram that is substantially the same in appearance as the DSC thermogram provided in FIG. 8.

17. A pharmaceutical composition comprising the crystalline form of zuclomiphene citrate of claim 11, and one or more pharmaceutically acceptable excipients.

18. The pharmaceutical composition of claim 17, wherein the pharmaceutical composition is a capsule or a tablet.

19. A process for the preparation of the crystalline form of zuclomiphene citrate of claim 11, the process comprising, combining zuclomiphene free base and citric acid in a solvent and crystallizing the zuclomiphene citrate using a condition selected from the group consisting of:
(1) combining the zuclomiphene free base and citric acid at a controlled rate;
(2) combining the zuclomiphene free base and citric acid at an elevated temperature; and
(3) maintaining the zuclomiphene citrate for a period of time.

20. The process of claim 19, wherein the solvent is an alkyl ester.

21. The process of claim 20, wherein the process comprises condition (1), (2), and (3).

22. The process of claim 19, wherein the elevated temperature is a temperature in the range of about 50° C. to about 70° C.

23. The process of claim 19, wherein the period of time is in the range of about 16 hours to about 48 hours.

* * * * *